United States Patent
Ramakrishnan et al.

(10) Patent No.: US 10,817,669 B2
(45) Date of Patent: Oct. 27, 2020

(54) AUTOMATIC CLASSIFICATION OF ADVERSE EVENT TEXT FRAGMENTS

(71) Applicant: International Business Machines Corporation, Armonk, NY (US)

(72) Inventors: Cartic Ramakrishnan, San Jose, CA (US); Pathirage D. S. U. Perera, San Jose, CA (US); Sheng Hua Bao, San Jose, CA (US); Vivek Krishnamurthy, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 100 days.

(21) Appl. No.: 16/246,895

(22) Filed: Jan. 14, 2019

(65) Prior Publication Data

US 2020/0226218 A1 Jul. 16, 2020

(51) Int. Cl.
*G06F 40/30* (2020.01)
*G06N 3/04* (2006.01)
(Continued)

(52) U.S. Cl.
CPC .............. *G06F 40/30* (2020.01); *G06N 3/04* (2013.01); *G06N 3/08* (2013.01); *G16H 50/20* (2018.01)

(58) Field of Classification Search
CPC .... G06F 16/353; G06F 16/355; G06F 40/289; G06F 40/30; G16H 50/70; G16H 50/20; G06N 3/04; G06N 3/08
See application file for complete search history.

(56) References Cited

U.S. PATENT DOCUMENTS

| 6,915,254 B1 | 7/2005 | Heinze et al. |
| 9,005,119 B2 | 4/2015 | Iliff |

(Continued)

FOREIGN PATENT DOCUMENTS

WO 2014201515 A1 12/2014

OTHER PUBLICATIONS

Kaushal, Daljeet Kaur, "A Development Environment to Integrate Big Data with Deep Learning," Thesis, Florida Institute of Technology, Jul. 2018, 104 pages.
(Continued)

*Primary Examiner* — Angela A Armstrong
(74) *Attorney, Agent, or Firm* — Will Stock; Edell, Shapiro & Finnan, LLC

(57) ABSTRACT

A method, a system, and a computer program product are provided. A training set of adverse event text fragments assigned to medical codes is analyzed to determine first text fragments having frequently occurring medical code assignments and second text fragments having infrequently occurring medical code assignments. The training set is modified to undersample the first text fragments and to oversample the second text fragments such that the text fragments of the modified training set correspond to a substantially uniform assignment of the medical codes. At least one machine learning model is generated and trained with the modified training set. Some parameters of the at least one machine learning model are updated based on errors detected during the training. After completing the training, an adverse event text fragment is applied to the at least one machine learning model to assign at least one medical code.

15 Claims, 5 Drawing Sheets

(51) Int. Cl.
*G06N 3/08* (2006.01)
*G16H 50/20* (2018.01)

(56) References Cited

U.S. PATENT DOCUMENTS

| | | | |
|---|---|---|---|
| 9,268,766 B2* | 2/2016 | Bekkerman | G06F 40/258 |
| 2004/0083224 A1* | 4/2004 | Yoshida | G06F 16/353 |
| 2005/0234955 A1* | 10/2005 | Zeng | G06F 16/355 |
| 2008/0059391 A1* | 3/2008 | Rosales | G16H 50/20 |
| | | | 706/12 |
| 2008/0177736 A1* | 7/2008 | Spangler | G06F 16/355 |
| 2008/0288292 A1* | 11/2008 | Bi | G06F 19/00 |
| | | | 705/3 |
| 2009/0055378 A1 | 2/2009 | Alecu et al. | |
| 2010/0094854 A1* | 4/2010 | Rouhani-Kalleh | |
| | | | G06F 16/3325 |
| | | | 707/706 |
| 2011/0213777 A1* | 9/2011 | Sun | G06F 16/353 |
| | | | 707/740 |
| 2013/0096170 A1 | 4/2013 | Garcia da Rocha et al. | |
| 2013/0226843 A1* | 8/2013 | Syeda-Mahmood | |
| | | | G16H 50/70 |
| | | | 706/12 |
| 2016/0063887 A1 | 3/2016 | Petritaj | |
| 2016/0078361 A1 | 3/2016 | Brueckner et al. | |
| 2017/0300829 A1 | 10/2017 | Iyengar et al. | |

OTHER PUBLICATIONS

Ding et al., "CIRCNN: Accelerating and Compressing Deep Neural Networks Using Block-Circulant Weight Matrices," Proceedings of the 50th Annual IEEE/ACM International Symposium on Microarchitecture, ACM, 2017, 14 pages.

Rouhani, Bita Darvish, "A Resource-Aware in Streaming-Based Framework for Big Data Analysis," Thesis, Rice University, 2015, 86 pages.

Yu et al., "Large Linear Classification When Data Cannot Fit in Memory," ACM Transactions on Knowledge Discovery from Data (TKDD) 5.4 (2012):23, 23 pages.

Zorzi et al., Mapping Free Text into MedDRA by Natural Language Processing: a Modular Approach in Designing and Evaluating Software Extensions, ACM-BCB'17, Boston, MA, Aug. 2017, 9 pages.

Disclosed Anonymously, "Confidence Score Assignment for Section-Level Evaluation and Management (E/M) Coding" IP.com Prior Art Database Technical Disclosure, IPCOM000243506D, Sep. 28, 2015, 5 pages.

Disclosed Anonymously, Hyperslice Confidence Estimation of ICD10-Procedure Coding System (ICD10-PCS) Codes and Constituent Concepts, IP.com Prior Art Database Technical Disclosure, IPCOM000229267D, Jul. 17, 2013, 16 pages.

Disclosed Anonymously, "Method and System of Classification of Images Based on Modality", IP.com Prior Art Database Technical Disclosure, IPCOM000218695D, Jun. 6, 2012, 6 pages.

\* cited by examiner

"use_word_embeddings": 1,
"use_char_embeddings": 0,

"max_sen_length": 100,
"make_word_embedding_trainable": 1,
"pretrained_word_embeddings": /path/filename.txt,
"pretrained_char_embeddings": null,
"word_embedding_dim": 300,
"char_embedding_dim": 25,
"max_char_in_word": 30, "kernel_config": "2:256, 3:128, 4:128",
"hidden_layers_dimes": "100",
"dropout_rate": 0.5

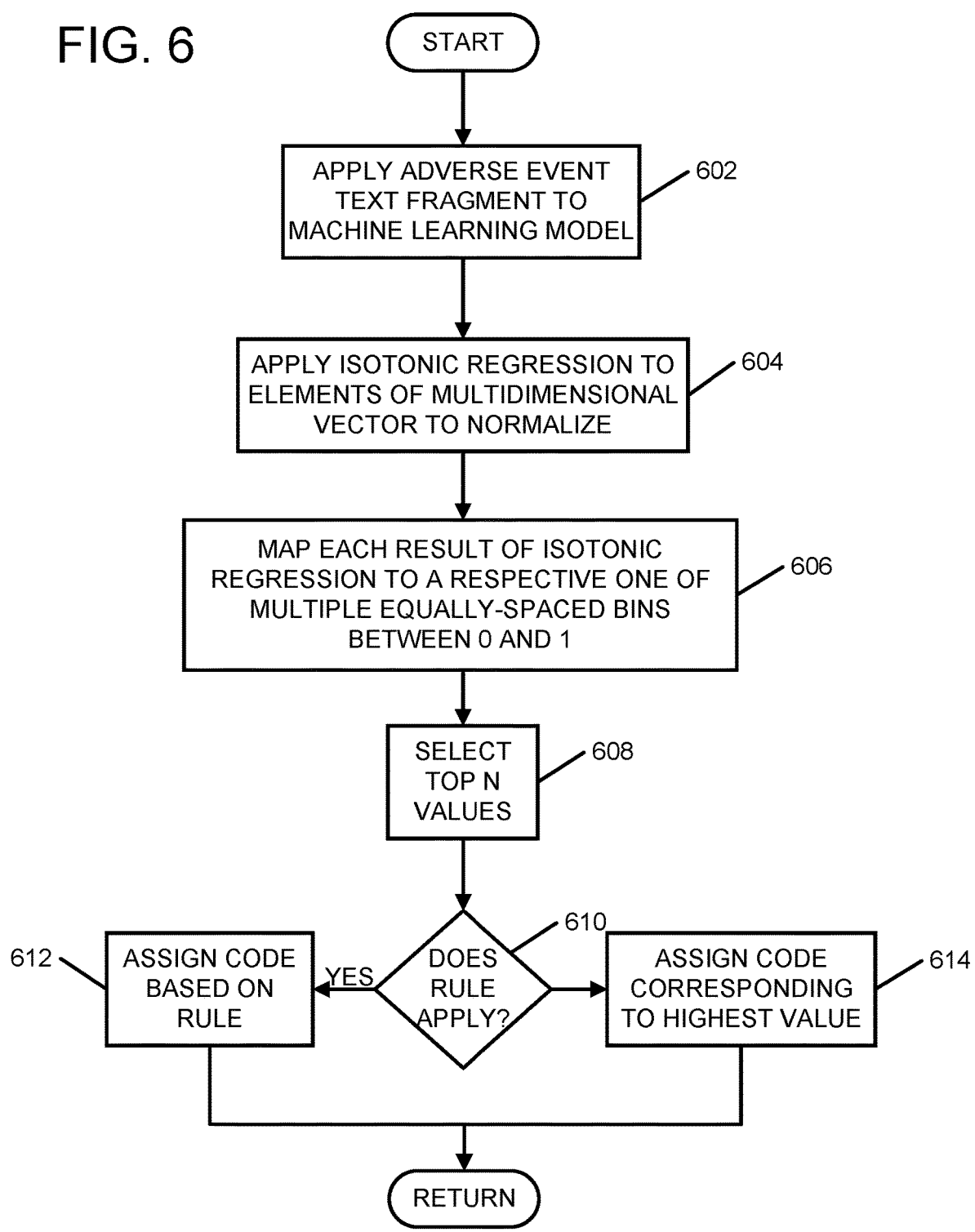

AUTOMATIC CLASSIFICATION OF ADVERSE EVENT TEXT FRAGMENTS

BACKGROUND

1. Technical Field

Present invention embodiments relate to building of one or more machine learning models for interpreting adverse event text fragments for classification into medical codes. In particular, the present invention embodiments relate to training of one or more machine learning models for automatically classifying adverse event text fragments into medical codes.

2. Discussion of the Related Art

Pharmacovigilance is the practice of monitoring effects of medical drugs after the drugs have been licensed for use. The monitoring is especially important with respect to identifying and evaluating previously unreported adverse events.

In the late 1990s, the International Council for Harmonization of Technical Requirements for Pharmaceuticals for Human Use (ICH) developed Medical Dictionary for Regulatory Activities (MedDRA), which is a rich and highly specific standardized medical terminology to facilitate sharing of regulatory information internationally for medical products used by humans.

MedDRA has a five-level hierarchical structure, arranged from very specific to very general. The most specific level is called "Lowest Level Terms" (LLTs), which includes more than 70,000 terms. A next level is called "Preferred Terms" (PTs), which is a distinct descriptor (single medical concept) for a symptom, sign, disease diagnosis, therapeutic indication, investigation, surgical or medical procedure, and medical social or family history characteristic. MedDRA includes over 22,000 PTs.

Currently, text narratives describing adverse events are manually classified, with assistance from autocoder programs, into medical codes including PTs and LLTs. Commercially available autocoder programs are procedural pattern-matching programs that facilitate exact match and synonym finding. However, these autocoder programs often fail when adverse events are reported in natural language. Further, because the commercial autocoder programs rely on using synonym lists, if a relevant synonym is missing from a synonym list, the autocoder programs will fail to assign a medical code.

SUMMARY

According to one embodiment of the present invention, a method of interpreting text fragments for classification of adverse events into medical codes is provided. A processor analyzes a training set of text fragments of adverse events assigned to the medical codes to determine frequently occurring assignments of the medical codes and infrequently occurring assignments of the medical codes. The processor modifies the training set to undersample first text fragments corresponding to the frequently occurring assignments of the medical codes and to oversample second text fragments corresponding to the infrequently occurring assignments of the medical codes such that the text fragments of the modified training set correspond to a substantially uniform assignment of the medical codes. The processor generates one or more machine learning models, each of which has multiple parameters. The one or more machine learning models are trained with the modified training set. The processor updates at least some of the multiple parameters of the one or more machine learning models based on errors detected during the training. After completing the training, the processor applies a text fragment pertaining to an adverse event to the one or more machine learning models to interpret the text fragment and assign one or more of the medical codes to the text fragment.

According to a second embodiment of the present invention, a system for interpreting text fragments for classification of adverse events into medical codes is provided. The system includes at least one processing device having at least one processor and a memory connected to the at least one processor. The at least one processing device is configured to analyze a training set of text fragments of adverse events assigned to medical codes to determine frequently occurring assignments of the medical codes and infrequently occurring assignments of the medical codes. The training set is modified to undersample first text fragments corresponding to the frequently occurring assignments of the medical codes and to oversample second text fragments corresponding to the infrequently occurring assignments of the medical codes such that the text fragments of the modified training set correspond to a substantially uniform assignment of the medical codes. One or more machine learning models are generated, wherein each of the one or more machine learning models has multiple parameters. The one or more machine learning models are trained with the modified training set. At least some of the multiple parameters of the one or more machine learning models are updated based on errors detected during the training. After completion of the training, a text fragment pertaining to an adverse event is applied to the one or more machine learning models to interpret the text fragment and assign one or more of the medical codes to the adverse event.

In a third embodiment of the present invention, a computer program product is provided. The computer program product includes at least one computer readable storage medium having computer readable program code embodied therewith for execution on at least one processor of a computing device. The computer readable program code is configured to be executed by the at least one processor to perform a number of steps. According to the steps, a training set of text fragments of adverse events assigned to medical codes are analyzed to determine frequently occurring assignments of medical codes and infrequently occurring assignments of the medical codes. The training set is modified to undersample first text fragments corresponding to the frequently occurring assignments of the medical codes and to oversample second text fragments corresponding to the infrequently occurring assignments of the medical codes such that the text fragments of the modified training set correspond to a substantially uniform assignment of the medical codes. One or more machine learning models having multiple parameters are generated. The one or more machine learning models are trained with the modified training set. At least some of the multiple parameters of the one or more machine learning models are updated based on errors detected during the training. After completion of the training, a text fragment pertaining to an adverse event is applied to the one or more machine learning models to interpret the text fragment and assign one or more of the medical codes to the adverse event.

BRIEF DESCRIPTION OF THE DRAWINGS

Generally, like reference numerals in the various figures are utilized to designate like components.

FIG. 6 is a flowchart of an example process that may be performed according to various embodiments to assign a medical code to a text fragment of an adverse event.

DETAILED DESCRIPTION

In various embodiments, one or more machine learning models may be trained to automatically classify adverse event text fragments into medical codes. In at least some embodiments, the medical codes may include PTs and LLTs of the MedDRA hierarchy and the one or more machine learning models may include a convolutional neural network. The trained one or more machine learning models may provide a confidence score for each possible medical code assignment, thereby providing an estimate of a degree of certainty that respective medical code assignments are correct based on past observations.

Figure 1:
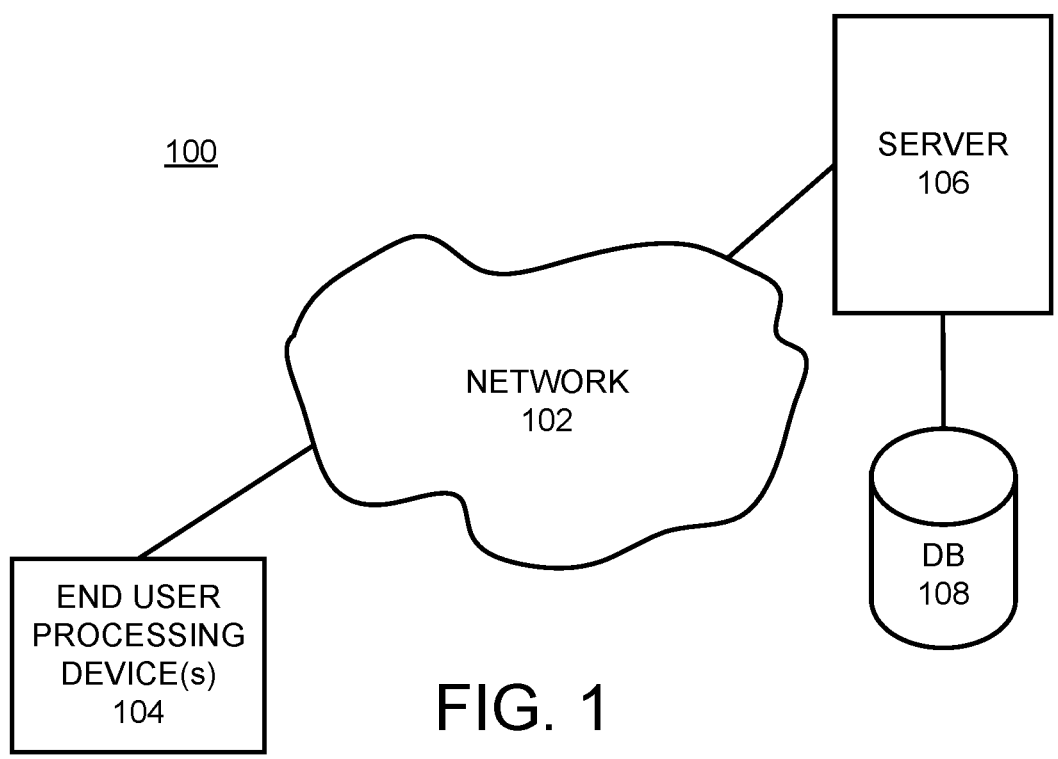
FIG. 1 shows an example operating environment according to embodiments of the invention.

An example environment 100 for use with present invention embodiments is illustrated in FIG. 1. Specifically, environment 100 may include one or more end user processing devices 104 and a server 106 connected to a network 102 either via a wired or a wireless connection. Server 106 further may be connected to a database 108, which may include a training set of data for training one or more machine learning models. In some embodiments, server 106 may include a server farm.

In some embodiments, instead of being connected to server 106, database 108 may be connected with a database server (not shown), which further may be connected to network 102.

End user processing device(s) 104 and server 106 may be remotely located from each other and may communicate via network 102. Network 102 may be implemented by any number of any suitable communications media (e.g., wide area network (WAN), local area network (LAN), Internet, Intranet, etc.). Alternatively, end user processing device(s) 104 and server 106 may be local to each other, and may communicate via any appropriate local communication medium (e.g., local area network (LAN), hardwire, wireless link, Intranet, etc.). In a standalone embodiment, end user processing device 104 may train the one or more machine learning models using the training set of data and may recommend medical codes to assign to adverse event text fragments by employing the one or more trained machine learning models.

End user processing device(s) 104 may be a handheld computing device, a tablet computer, a smartphone, a laptop computing device, a desktop computing device, or other type of computing device.

Server 106 may include a laptop computing device, a desktop computing device, a tablet computing device, or other type of computing device.

In some embodiments, after the one or more machine learning models are trained, end user processing device(s) 104 may provide one or more adverse event text fragments (e.g., natural language, verbatim, etc.) to server 106, which may include the one or more machine learning models. Server 106 may apply the one or more adverse event text fragments to the one or more trained machine learning models to assign the text fragments to one or more medical codes, which may be returned to end user processing device(s) 104. Alternatively, end user processing device(s) 104 may use the one or more trained machine learning models residing thereon to assign the one or more of the medical codes to the text fragments.

Figure 2:
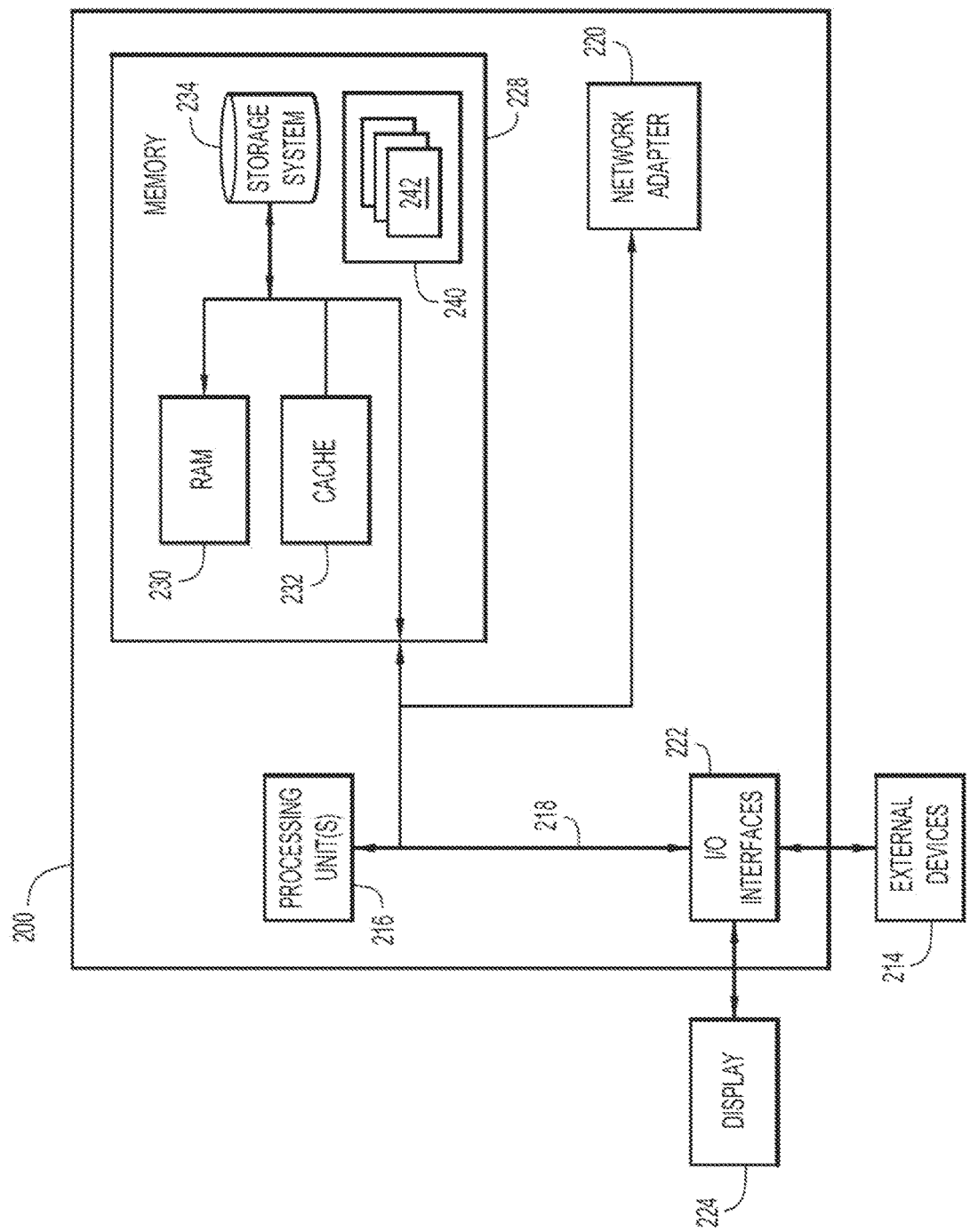
FIG. 2 is a functional block diagram of a general purpose computer for implementing embodiments of the invention.

Referring now to FIG. 2, a schematic of an example computer system 200 is shown, which may implement end user processing device 104 or server 106 in various embodiments. Computer system 200 is shown in a form of a general-purpose computing device. Components of computer system 200 may include, but are not limited to, one or more processors or processing units 216, a system memory 228, and a bus 218 that couples various system components including system memory 228 to one or more processing units 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 200 may include a variety of computer system readable media. Such media may be any available media that is accessible by computer system 200, and may include both volatile and non-volatile media, removable and non-removable media.

System memory 228 can include computer system readable media in the form of volatile memory, such as random access memory (RAM) 230 and/or cache memory 232. Computer system 200 may further include other removable/non-removable, volatile/non-volatile computer system storage media. By way of example only, storage system 234 can be provided for reading from and writing to a non-removable, non-volatile magnetic medium (not shown, which may include a "hard drive" or a Secure Digital (SD) card). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computer system 200 may also communicate with one or more external devices 214 such as a keyboard, a pointing device, one or more displays 224, one or more devices that enable a user to interact with computer system 200, and/or any devices (e.g., network card, modem, etc.) that enable computer system 200 to communicate with one or more other computing devices. Such communication can occur via Input/Output (I/O) interfaces 222. Still yet, computer system 200 can communicate with one or more networks such as a local area network (LAN), a general wide area network (WAN), and/or a public network (e.g., the Internet) via network adapter 220. As depicted, network adapter 220 communicates with the other components of computer system 200 via bus 218. It should be understood that, although not shown, other hardware and/or software components could be used in conjunction with computer system 200. Examples, include, but are not limited to: a microphone, one or more speakers, microcode, device drivers, redundant processing units, external disk drive arrays, RAID systems, tape drives, and data archival storage systems, etc.

Figure 3:
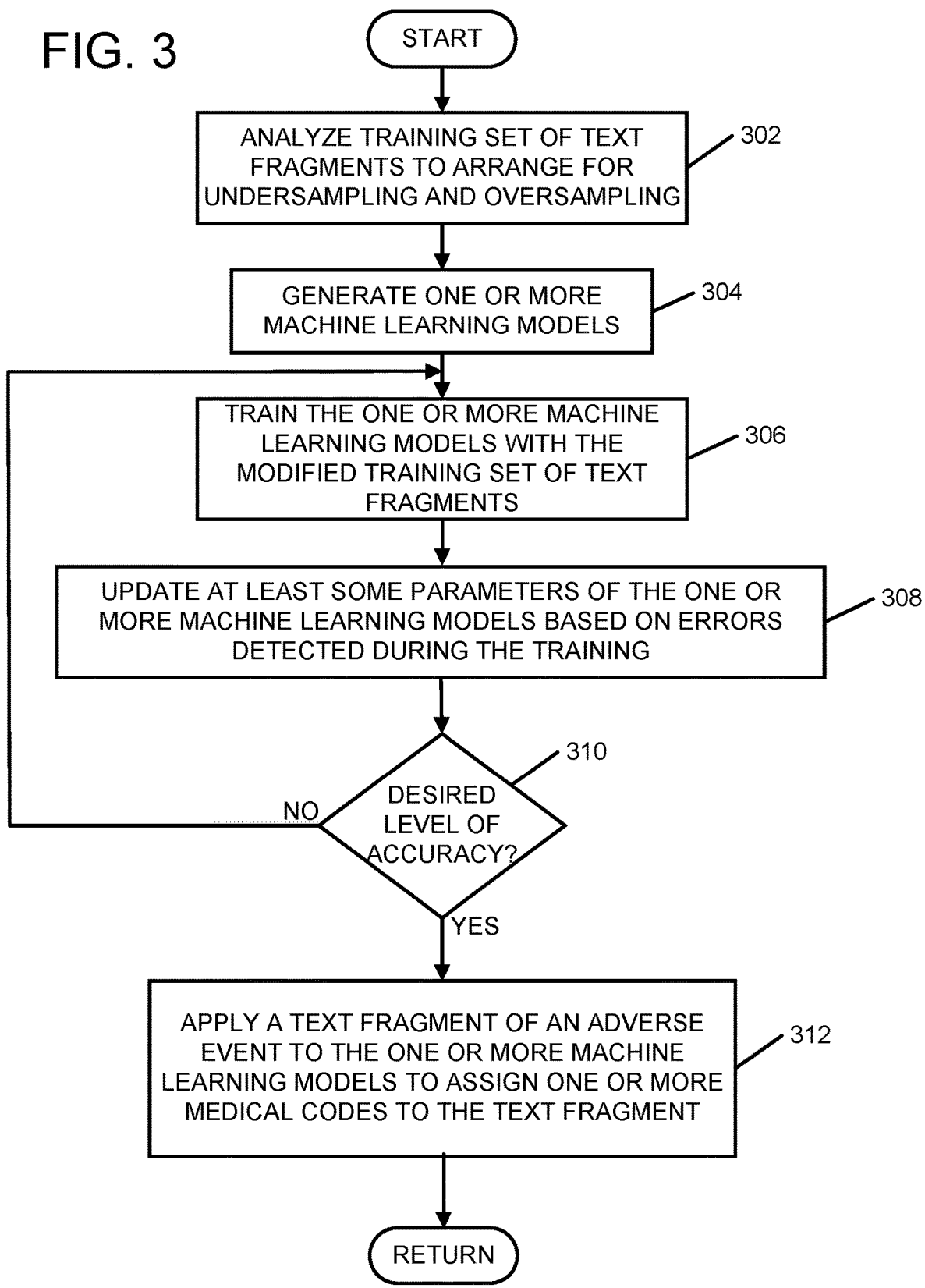
FIG. 3 is a flowchart illustrating an example process that may be performed according to various embodiments to train and use one or more machine learning models.

FIG. 3 is a flowchart that illustrates an example process that may be performed in a computing device such as, for example, end user processing device 104 or server 106 according to embodiments of the invention. The process may begin by analyzing a training set of adverse event text fragments (e.g., natural language, verbatim, etc.) to determine frequently occurring assignments of medical codes and infrequently occurring assignments of the medical codes and modify the training set to undersample first text fragments corresponding to the frequently occurring assignments of the medical codes and oversample second text fragments corresponding to the infrequently occurring assignments of the medical codes such that the text fragments in the modified training set correspond to a substantially uniform assignment of the medical codes (act 302). This may be achieved by modifying the training set to add instances of the second text fragments to the training set and decreasing instances of the first text fragments in the training set.

Next, one or more machine learning models may be generated for assigning one or more medical codes to an adverse event text fragment (act 304). The one or more medical codes may include LLTs and PTs of MedDRA. In some embodiments, a first machine learning model may be specified for assigning LLTs to adverse event text fragments and a second machine learning model may be specified for assigning PTs to adverse event text fragments. In various embodiments, TensorFlow® (TensorFlow is a registered trademark of Google Inc., with headquarters in Mountain View, Calif.) may be used to specify the one or more machine learning models, which TensorFlow® may generate.

TensorFlow® is an open source library developed for high performance numerical computation. TensorFlow® allows developers to create a dataflow graph that describes how data moves through the graph. The graph includes a series of processing nodes, each of which represents a mathematical operation. Each edge between nodes is a multidimensional data array, or tensor.

The one or more machine learning models may be trained using the training set including the undersampled and over-sampled adverse event text fragments as described above (act 306). In at least some embodiments, the one or more machine learning models may include a convolutional neural network (CNN).

After an iteration of training with the training set, parameters or weights of the one or more machine learning models may be updated based on errors detected during the iteration of training (act 308). That is, the parameters may be adjusted to decrease a value of a loss function. One common loss function that may be used in various embodiments is a mean squared error, which is a sum of ½ of differences of each actual result from a corresponding predicted result squared.

$$E_{total}=\Sigma \frac{1}{2}(actual-predicted)^2$$

In other embodiments, a different loss function may be used.

Acts 306 and 308 represent one training iteration. Accuracy of the one or more machine learning models may be determined by using the or more machine learning models to assign medical codes to adverse event text fragments of another set of data that had already previously been assigned to correct medical codes and determining a percentage of correct or incorrect medical codes assigned to the adverse event text fragments by the one or more machine learning models. FIG. 6, which will be discussed below, shows a flowchart of an example process for applying an adverse event text fragment to a machine learning model to assign a medical code. If a desired level of accuracy is not yet achieved by the one or more machine learning models, then acts 306 and 308 may be repeated to perform another iteration of training. If, during act 310, a determination is made that the one or more machine learning models has reached or exceeded the desired level of accuracy, then the training of the one or more machine learning models is completed and adverse event text fragments may be applied to the one or more machine learning models to assign one or more medical codes thereto (act 312).

In order to train a machine learning model to assign a medical code to an adverse event text fragment, words of text fragments may be assigned to respective multidimensional vectors. In some embodiments, each unique word of the adverse event text fragments may be assigned to an n-dimensional vector, where n may be 300, 500, 1,000, or another suitable value. Each element of each n-dimensional vector may initially have a randomly assigned value in a range of 0.0 to 1.0. So, for example, if there are 10,000 unique words in a training set of adverse event text fragments, then each of the 10,000 unique words will be assigned to a respective n-dimensional vector having elements with randomly assigned real values between 0.0 and 1.0. During training of the one or more machine learning models, co-occurrences of words with other words appearing within a fixed number of words in adverse event text fragments may be analyzed to adjust values of the n-dimensional vectors such that words having similar meanings have corresponding similar n-dimensional vectors and words having very different meanings have very different corresponding n-dimensional vectors.

In other embodiments, each unique word of the adverse event textual fragments of the training set may be assigned a corresponding n-dimensional vector based on other methods. Any of a number of known methods may be used to assign a corresponding unique n-dimensional vector to each of the unique words.

Figures 4, 5:
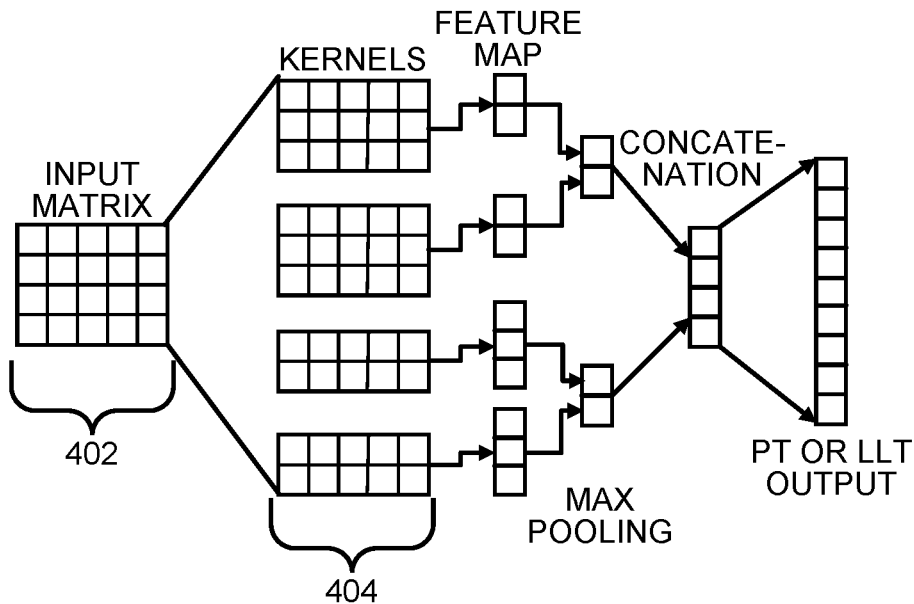
FIG. 4 shows an example convolutional neural network that may implement a machine learning model according to various embodiments.
FIG. 5 illustrates settings that may be used to generate a convolutional neural network for a machine learning model according to some embodiments.

In at least some embodiments, TensorFlow® may be used to specify a structure of a CNN for assigning a medical code to an adverse event text fragment. FIG. 4 illustrates an example structure of a CNN for a machine learning model for assigning either a PT or a LLT to an adverse event text fragment. In some embodiments, one machine learning model may be trained to assign PTs to adverse event text fragments and a second machine learning model may be trained to assign LLTs to adverse event text fragments.

Each row of an input matrix 402 may include an n-dimensional vector representation of a word of an adverse event text fragment such as, for example, "throbbing pain in head" or another adverse event text fragment. Kernels 404 may be applied to input matrix 402 to produce feature maps. In this example, assume that an adverse event text fragment includes four words. A top two kernels in FIG. 6 may have three rows, which may be applied to a sliding window of three word vectors. A top three word vectors, corresponding to, for example, "throbbing pain in", may be applied to a top kernel 404 to produce one output of a feature map and a bottom three word vectors, corresponding to, for example, "pain in head" may be applied to the top kernel 404 to produce a second output of the feature map. Similarly, the top three word vectors may be applied to a second kernel 404 (second kernel from the top) to produce one output of a second feature map and a bottom three word vectors may be applied to the second kernel 404 to produce a second output of the second feature map. A third kernel 404 may be applied to the first two word vectors of input matrix 402 to produce a first output of a feature map, the third kernel 404 may be applied to the second and third word vectors of input matrix 402 to produce a second output of the second feature map, and the third kernel 404 may be applied to the third and fourth word vectors of input matrix 402 to produce a third output of the second feature map. A fourth kernel 404 may be applied to the word vectors of input matrix 402 in a same manner as the third kernel to produce three outputs of a fourth feature map.

Next, max pooling may be performed on the feature maps to reduce a spatial size of a representation of the feature maps.

The results of max pooling may be concatenated to produce a concatenated result, which may be applied to a fully connected layer to produce a multidimensional vector such that each element of the multidimensional vector corresponds to a different PT medical code or a different LLT medical code and the value of each of the elements is between 0 and 1 and corresponds to a confidence score, or probability, that the corresponding medical code is a correct medical code based on past observations. In some embodiments, one CNN may produce a multidimensional vector having elements corresponding to PTs and another CNN may produce a multidimensional vector having elements corresponding to LLTs.

As previously mentioned, TensorFlow® may be used to specify the one or more machine learning models as CNNs. FIG. 5 illustrates an example setting of parameters for TensorFlow® to generate a CNN. For example, "use_word_settings" may be set to 1 to indicate that the CNN is to use word vectors. "Use_char_embeddings" may be set to 0 to indicate that the CNN will not use character vectors to represent characters. "Max_sen_length" may be set to 100 to indicate a maximum word length of an adverse event text fragment. "Make_word_embedding_trainable" may be set to 1, indicating that word vectors are trained based on unique words appearing in the adverse event text fragments and co-occurrences of the unique words with other words in the adverse event text fragments. "Pretrained_word_embeddings" is an optional parameter that indicates a path and file name of a file that includes pretrained word vectors. "Word_embedding_dim" may be set to 300 to indicate that word vectors are 300-dimensional vectors. "Char_embedding_dim" may be set to 25, but since "use_char_embeddings" is set to 0, indicating that character vectors are not used, "char_embedding_dim" will not be used. "Max_char_in_word" may be set to 30 to indicate that a maximum length of a word is 30 characters. "Kernel_config" may be set to "2:256, 3:128 and 4:128". "Hidden_layers-dimens" may be set to 100, indicating that no more than 100 nodes may be included in the hidden layers of a CNN. "Dropout_rate" may be set to 0.5 indicating that 50% of input units are to be randomly set to zero at each update during training in order to help prevent overfitting.

As indicated above by the setting of "make_word_embedding_trainable" to 1, word vector representations of each word of the adverse event may be trained by the CNN generated by TensorFlow®. Based on the above settings, the trained word vectors may be 300-dimensional vectors such that words having similar meanings have similar 300-dimensional vectors and words having very different meanings have very different 300-dimensional vectors.

The multidimensional vector result of a CNN for a machine learning model may include many values that are near 0.0 or near 1.0 such as, for example, 0.0001 or 0.9999. In various embodiments, the values of the multidimensional vector result of a machine learning model may be normalized, or calibrated, to spread out the values. One method of normalizing, or calibrating, the values of the multidimensional vector result may include using isotonic regression.

Isotonic regression fits a free form line of a graph to a sequence of observations subject to constraints that include: the fitted free form line being non-decreasing everywhere; and the free form line lying as close as possible to the sequence of observations. In some embodiments, the respective normalized values may be mapped to one of multiple bins that are equally spaced between a value of 0 and 1 inclusive. In some embodiments, the respective normalized values may be mapped to one of between five and ten equally spaced bins between 0 and 1 inclusive. Each bin corresponds to a respective non-decreasing value. Thus, for example, when 5 equally spaced bins are used, values produced by using isotonic regression may be mapped such that values that are greater than or equal to 0 and less than 0.2 may be mapped to 0.1, values that are greater than or equal to 0.2 and less than 0.4 may be mapped to 0.3, values that are greater than or equal to 0.4 and less than 0.6 may be mapped to 0.5, values that are greater than or equal to 0.6 and less than 0.8 may be mapped to 0.7, and values that are greater than or equal to 0.8 and less than or equal to 1.0 may be mapped to 0.9.

FIG. 6 is a flowchart illustrating an example process for assigning a medical code to an adverse event text fragment via a trained machine learning model. The process may begin by applying the adverse event text fragment to the machine learning model, which may produce an n-dimensional vector result (act 602). Each element of the n-dimensional vector corresponds to a respective medical code and has a value indicating a level of certainty that the corresponding respective medical code is a correct medical code.

Next, isotonic regression may be applied to the values of the elements of the n-dimensional vector to normalize the values (act 604). Each of the normalized values may be mapped to a respective one of multiple equally-spaced bins between 0 and 1, as previously described (act 606). Various embodiments may include between 5 and 10 equally-spaced bins.

From the normalized and binned values, a top, or highest, N values may be selected, where N may be 4, 5 or another suitable value (act 608). Next, a determination may be made regarding whether a rule is to be applied regarding the adverse event text fragment (act 610). In some embodiments, an input adverse event text fragment may be compared against a number of rules, each of which may determine whether the adverse event text fragment includes one or more particular words, one or more particular phrases, or one or more combinations of certain words.

If the input adverse event text fragment satisfies a rule, the satisfied rule indicates which of the N values, other than a highest of the N values, is a best of the N values corresponding to a medical code to assign (act 612). For example, if the input adverse event text fragment satisfies a particular rule, a medical code corresponding to a second highest of the N values may be assigned. Otherwise, a medical code corresponding to a highest of the N normalized, binned values may be assigned (act 614). The values of elements of the multidimensional vector result indicate a level of certainty that a corresponding medical code is a correct medical code based on past observations.

As mentioned above, words included in adverse event text fragments may be represented by respective multidimensional vectors. In some embodiments the multidimensional vectors may be 300 dimensional vectors. In other embodiments, the multidimensional vectors may be 500 dimensional vectors or may have another number of dimensions.

It will be appreciated that the embodiments described above and illustrated in the drawings represent only a few of the many ways of implementing embodiments for training one or more machine learning models to assign one or more medical codes to respective adverse event text fragments.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, profile generation module, profile comparison module, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., knowledge base, units of work, action graphs, critical path graphs, etc.). The database system may be implemented by any number of any conventional or other databases, data stores or storage structures to store information. The database system may be included within or coupled to a server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method of interpreting text fragments for classification of adverse events into medical codes comprising:
   analyzing, via a processor, a training set of text fragments of adverse events assigned to the medical codes to determine frequently occurring assignments of the medical codes and infrequently occurring assignments of the medical codes;
   modifying, via the processor, the training set to undersample first text fragments corresponding to the frequently occurring assignments of the medical codes and to oversample second text fragments corresponding to the infrequently occurring assignments of the medical codes such that the text fragments of the modified training set correspond to a substantially uniform assignment of the medical codes;
   generating, via the processor, one or more machine learning models, each of the one or more machine learning models having a plurality of parameters;
   training, via the processor, the one or more machine learning models with the modified training set;
   updating, via the processor, at least some of the plurality of parameters of the one or more machine learning models based on errors detected during the training; and
   applying, via the processor after completion of the training, a text fragment pertaining to an adverse event to the one or more machine learning models to interpret the text fragment and assign one or more of the medical codes to the adverse event, the applying further comprising:
      normalizing, by the processor, values of elements of a multidimensional vector produced by applying the text fragment to one of the one or more machine learning models and mapping each of the normalized values to a respective bin of a plurality of bins, the plurality of bins being equally spaced between a value of 0 and 1 inclusive, each of the elements corresponding to a respective medical code, and a respective value of the each of the elements indicating a level of certainty that the corresponding respective medical code is a correct medical code, wherein
   the one or more machine learning models include a convolutional neural network.

2. The method of claim 1, wherein the convolutional neural network assigns to words of the text fragments respective multidimensional vector representations of the words.

3. The method of claim 1, wherein the one or more machine learning models are specified using TensorFlow.

4. The method of claim 1, further comprising:
   performing, by the processor, a plurality of training iterations, wherein parameters for layers of the convolutional network are updated, after each of the plurality of training iterations to minimize a loss function for the layers.

5. The method of claim 1, wherein the normalizing further comprises:
   using isotonic regression to map the each of the normalized values of the elements of the multidimensional vector to the respective bin of the plurality of bins.

6. The method of claim 1, further comprising:
   selecting a plurality of highest values based on the values of the elements of the multidimensional vector;
   determining that the text fragment satisfies one of a plurality of rules; and
   selecting one of the plurality of highest values according to the satisfied one of the plurality of rules; and
   assigning a medical code to the text fragment corresponding to the selected one of the plurality of highest values.

7. A system for interpreting text fragments for classification of adverse events into medical codes, the system comprising:
   at least one processing device, each of the at least one processing device comprising:
      at least one processor, and
      a memory connected to the at least one processor, wherein
      the at least one processing device is configured to:
         analyze a training set of text fragments of adverse events assigned to the medical codes to determine frequently occurring assignments of the medical codes and infrequently occurring assignments of the medical codes;
         modify the training set to undersample first text fragments corresponding to the frequently occurring assignments of the medical codes and to oversample second text fragments corresponding to the infrequently occurring assignments of the medical codes such that the text fragments of the modified training set correspond to a substantially uniform assignment of the medical codes;
         generate one or more machine learning models, each of the one or more machine learning models having a plurality of parameters;
         train the one or more machine learning models with the modified training set;
         update at least some of the plurality of parameters of the one or more machine learning models based on errors detected during the training; and
         apply, after completion of the training, a text fragment pertaining to an adverse event to the one or more machine learning models to interpret the text fragment and assign one or more of the medical codes to the adverse event, the at least one processing device being configured to apply the text fragment to the adverse event further comprising the at least one processing device being configured to:
            normalize values of elements of a multidimensional vector produced by applying the text fragment to one of the one or more machine learning models and mapping each of the normalized values to a respective bin of a plurality of bins, the plurality of bins being equally spaced between a value of 0 and 1 inclusive, each of the elements corresponding to a respective medical code, and a respective value of the each of the elements indicating a level of certainty that the corresponding respective medical code is a correct medical code, wherein the one or more machine learning models include a convolutional neural network.

8. The system of claim 7, wherein the one or more machine learning models are specified using TensorFlow.

9. The system of claim 7, wherein the at least one processing device is further configured to:

perform a plurality of training iterations, wherein parameters for layers of the convolutiona1 network are updated after each of the iterations to minimize a loss function for the layers.

10. The system of claim 7, wherein the at least one processing device being configured to normalize the values of the multidimensional vector further comprises the at least one processing device being configured to:

use isotonic regression to map the each of the normalized values of the elements of the multidimensional vector to the respective bin of the plurality of bins.

11. The system of claim 7, wherein the at least one processing device is further configured to:

select a plurality of highest values based on the values of the elements of the multidimensional vector;

determine that the text fragment satisfies one of a plurality of rules; and select one of the plurality of highest values according to the satisfied one of the plurality of rules; and assign a medical code to the respective text fragment corresponding to the selected one of the plurality of highest values.

12. A computer program product comprising at least one computer readable storage medium having computer readable program code embodied therewith for execution on at least one processor of a computing device, the computer readable program code being configured to be executed by the at least one processor to perform:

analyzing a training set of text fragments of adverse events assigned to medical codes to determine frequently occurring assignments of medical codes and infrequently occurring assignments of the medical codes;

modifying the training set to undersample first text fragments corresponding to the frequently occurring assignments of the medical codes and to oversample second text fragments corresponding to the infrequently occurring assignments of the medical codes such that the text fragments of the modified training set correspond to a substantially uniform assignment of the medical codes;

generating one or more machine learning models, each of the one or more machine learning models having a plurality of parameters;

training the one or more machine learning models with the modified training set;

updating at least some of the plurality of parameters of the one or more machine learning models based on errors detected during the training; and applying, after completion of the training, a text fragment pertaining to an adverse event to the one or more machine learning models to interpret the text fragment and assign one or more of the medical codes to the adverse event, the applying further comprising:

normalizing values of elements of a multidimensional vector produced by applying the text fragment to one of the one or more machine learning models and mapping each of the normalized values to a respective bin of a plurality of bins, the plurality of bins being equally spaced between a value of 0 and 1 inclusive, each of the elements corresponding to a respective medical code, and a respective value of the each of the elements indicating a level of certainty that the corresponding respective medical code is a correct medical code, wherein the one or more machine learning models include a convolutional neural network.

13. The computer program product of claim 12, wherein the one or more machine learning models are specified by using TensorFlow.

14. The computer program product of claim 12, wherein the computer readable program code is further configured to be executed by the at least one processor to perform:

using isotonic regression to map the each of the normalized values of the elements of the multidimensional vector to the respective bin of the plurality of bins.

15. The computer program product of claim 12, wherein in the convolutional neural network single words of the text fragments are represented by respective multidimensional vectors produced by the convolutional neural network.

* * * * *